United States Patent
Albert et al.

(10) Patent No.: US 8,815,948 B2
(45) Date of Patent: Aug. 26, 2014

(54) HIGH VOLUME AND ALTERNATIVE METHODS OF DELIVERING HOMEOPATHIC REMEDIES

(75) Inventors: Char Tara Albert, Vero Beach, FL (US); Floyd E. Taub, Silver Spring, MD (US)

(73) Assignee: Dovetail Technologies, Inc.

( * ) Notice: Subject to any disclaimer, the term of this patent is extended or adjusted under 35 U.S.C. 154(b) by 1523 days.

(21) Appl. No.: 11/054,093

(22) Filed: Feb. 10, 2005

(65) Prior Publication Data

US 2008/0039523 A1 Feb. 14, 2008

Related U.S. Application Data

(60) Provisional application No. 60/544,181, filed on Feb. 13, 2004.

(51) Int. Cl.
*A61K 31/315* (2006.01)
*A61K 31/24* (2006.01)
*A61K 45/00* (2006.01)

(52) U.S. Cl.
USPC ........... 514/553; 514/528; 514/885; 514/494; 514/534; 514/789; 424/600

(58) Field of Classification Search
USPC ................ 514/553, 528, 885, 494, 534, 789; 424/600, 725, 450, 464, 541
See application file for complete search history.

(56) References Cited

U.S. PATENT DOCUMENTS 6,007,819 A * 12/1999 Taub et al. .................. 424/184.1
2004/0019107 A1 * 1/2004 Taub et al. .................... 514/553

* cited by examiner

*Primary Examiner* — Savitha Rao
(74) *Attorney, Agent, or Firm* — Julie L. Bernard, LLC

(57) ABSTRACT

An alternative method of delivery of homeopathic medicines by targeting delivery to the MALT's, especially of the intestinal tract and in high volumes.

14 Claims, No Drawings

HIGH VOLUME AND ALTERNATIVE METHODS OF DELIVERING HOMEOPATHIC REMEDIES

FIELD OF THE INVENTION

This invention relates to alternative methods of delivering homeopathic remedies, especially of high volume homeopathic remedies.

BACKGROUND OF THE INVENTION

The current accepted method of delivering homeopathic remedies designed for systemic effects is sub-lingual administration and/or small portions. (Salves or gels are also used for local administration.)

Sublingual administration either in the form of small amounts of liquid tinctures or pellets or lozenges that dissolve in the mouth is extensively described.

The literature reports the mouth should be clean and free of other materials to allow for effective absorption through the oral mucosa. Usually any food intake for 15 minutes before or after is prohibited or at least discouraged. Nasal or rectal delivery is rarely used, this again only with small volumes. Rarely remedies containing large amounts of drug are diluted with 1-2 cups of water within 12 hours of consumption.

The essence of this invention is that homeopathic remedies, containing relatively few molecules 4× and 5× and above solutions, especially but not limited to ones known to act via the immune system may be made well in advance in large volumes and delivered by other methods. The entire G.I. tract is lined, just below and sometimes contained within the mucosa (the innermost lining), with a rich supply of individual, small groups, and large collections of lymphocytes. Thus a homeopathic remedy delivered to these sites has excellent potential to almost immediately interact with lymphoid cells (or other cells, especially glandular and absorptive gastro intestinal cells) and to start a cascade of events leading to a decrease in disease or alteration of physiologic state. The liver may also alter a prodrug to a metabolically active form (or relatively confine a relatively toxic prodrug to the portal circulation) so this first pass through the liver may be very important; upon being picked up by the blood stream, the mesenchymal and portal circulations first deliver the absorbed materials to the liver and spleen which are extraordinarily important to immune function. In addition, this invention allows more direct and specific delivery to mesenteric lymph nodes, liver and spleen. Delivery to one or all of these organs is especially important for certain diseases such as hepatitis or others affecting these organs. The liver and spleen are two of the largest immunologic organs in the body. In addition the liver has numerous detoxification and synthetic functions that are essential for optimizing health and curing disease; an initial "first" pass through these organs is likely to optimize the bioactivity. Thus, we have discovered that, contrary to current and long-held beliefs in the art and in the literature of homeopathy, delivery to the stomach, small intestine and most of the large intestine of dilute homeopathic remedies can be extremely beneficial. This contrasts to the blood flow from the oral mucosa.

Thus, contrary to current and long-held beliefs in the art and literature of homeopathy, we have discovered 1. that delivery to G.I. Tract distal to the oropharynx and proximal to the rectum is possible (by one of several methods), 2. homeopathic products, especially these homeopathic products, may be taken without the need for special "clean" mouth, (or limiting food and water intake, or restricting foods previously restricted, especially certain agents like mints-flavor which were especially forbidden), and 3. distal delivery may be more advantageous in some situations.

Also, contrary to current and long-held beliefs in the art and in the literature of homeopathy, we have discovered that delivery in large volumes of liquid (anything over a teaspoon or certainly over a tablespoon) is possible so that according to this invention delivery is possible and advantageous without the need for a special "clean" mouth, i.e., without being limited with respect to food and water intakes before and after the administration of the preparation, without the need to keep the preparation in the mouth for any period of time (typically 15-90 seconds) and without the requirement not to have any food within minutes to hours as well as without the requirement to entirely avoid certain forbidden agents such as mint flavors. In fact, the preparation may be taken mixed with pleasant-tasting beverages like juices, health drinks, water or other drinks.

We have also discovered that even when large volumes are not used, delivery to the stomach and to the intestines can be most advantageous. Encapsulation and other strategies allowing delivery specifically to the stomach, the small intestine and to the large intestine has been discovered to be extremely beneficial. Historically some practitioners who give oral preparations of materials that, had they been prepared as homeopathic preparations and given sublingual, would be homeopathic and, are considered naturopathic or nutritional practitioners. They typically require delivery of much higher doses and lack the micro-medicine benefits of homeopathy. These naturopathic methods are very distinct from homeopathic methods in that they do not use succusion to activate and "potentize" the preparation. Vaginal and anal suppositories have been used but generally not as homeopathics, even if some examples of "homeopathic" uses exist, the homeopathic suppositories still tended to be of small volumes. It is also significant that the blood flow to these regions is different from the blood flow to the stomach, the small intestinal tract and even the large intestinal tract because it is not the same as the blood flow to the portal system. Anal and especially vaginal suppositories are more equivalent to local skin salves used heretofore than to a systemic stomach or to an intestinal method of administering homeopathic medicines as described in the instant application.

DESCRIPTION OF THE INVENTION

Without being limited by theory or by the following description, one of the distinguishing features of this invention, generally speaking, is its reliance on a G.I. delivery in contrast to the prior art.

The amount of lymphoid tissue associated with the mucosal soft tissue lining the oropharynx, stomach, large and small intestines, has been given the name Mucosal Associated Lymphocytic Tissues (MALT). This invention embodies new ways to deliver homeopathic medicines to MALT distal to the oropharynx. The homeopathic(s) may be in the form of suspensions, solutions, tablets, capsules (with coatings of various types), lipid containing capsules or micelles, or microspheres, or microspheres or buckyballs or any other pharmaceutical delivery devices or carriers now known in the standard pharmaceuticals literature or developed for the future. The blood from the intestines flows through the mesenchymal circulation to the liver and to the spleen which are major immunological organs containing a variety of immune cells. (See Paul, "Fundamentals of Immunology," incorporated herein by reference.)

In one embodiment of this invention all of the aforementioned regions of the body with MALTs (other than the oropharynx, anus and vagina) as well as any other regions of the body with MALTs, especially of the digestive system, are within the scope of this invention.

In this invention the homeopathic material may be mixed with other ingredients known in the pharmaceutical or nutraceutical practice now known or as known n the future to facilitate penetration or increase the efficacy and safety of the homeopathic drug or to complement the benefit.

Through a variety of methods, known in the allopathic pharmaceutical art, such as enteric coating, micro spheres, micelles, capsules with various coatings and of various materials and many combinations of lipids, or various types with each other and aqueous solutions can result in preparations designed for delivery as a remedy to virtually any part of the alimentary tract. These preparations themselves have some significant bulk but most importantly they are taken with larger amounts of carrier such as milk, water or juice. The homeopathic element thus may be homogeneous in the large carrier or taken contemporaneously.

Delivery by this method has distinct advantages when the disease to be treated may be located more distally to the oropharynx, especially in the alimentary tract such as inflammatory bowel disease, Crohn's Disease, proliferative diseases, inflammatory diseases, ulcerative diseases, atrophic diseases or other ailments of tissue in the region of the MALT or directly to the diseases of the mucosal tissues.

Another embodiment of this invention resides in the use of the gut associate MALT to absorb the homeopathic remedy for delivery to organs which receive portal circulation and also to the systemic organs to which the circulation ultimately goes, for example, following metabolic conversion in the liver before reaching the general circulation.

This invention applies equally to homeopathics at low and high potencies from 1× to 500 Million.

A common use might be locally made (by a person or soda fountain type machine) or especially prepackaged drinks containing volumes from ¼ cup to hundreds of gallons. Typically prepackaged drinks would be sold to the consumer in volumes of ¼ cup to 5 gallons. These might be labeled, for example, to alleviate fatigue, improve concentration, increase endurance or, without limitation, any of the other indications for any ailment for which any homeopathic remedy treats or prevents. These are listed in compendium of materia medica and incorporated herein by reference. A specific example is including in water homeopathic reagents known to stimulate the immune system and/or relieve fatigue.

Examples of homeopathic remedies that may be used, without limitation include, Taurox SB™, Tauroxicum, COBAT, TaurImmune all the products listed in the HPUS (Homeopathic Pharmacopeias of the United States), pharmacopeias of Germany or France or other agents which become so listed or otherwise established as homeopathic remedies ex HPUS. They also include those in homeopathic pharmacopeias of other countries and other medicines designated as homeopathic. (All these Pharmacopeias are included by reference in his application.) Other common homeopathic ingredients include aloe; armica; cactus; Licopodium and calceolaria. Numerous reference materials describing individual remedies and combinations of various remedies for various conditions, including Dana Ulman's Internet ebook are readily available to obviate the need for any undue experimentation for an effective remedy. Moreover, uses and applications of homeopathic remedies of interest are well described in the literature.

Examples of diseases or conditions that might be treated include all those mentioned in the monographs of the above or described in materia medicas and pharmacopeias well known to those in the homeopathic art. (This reference material is included in this disclosure by reference.) Infectious, cancerous, immunologic, post and preoperative, viruses, HIV/AIDS/Hepatitis, rhinoviruses (colds), and Flu in animals of people are a few examples for which the administration according to this invention is applicable, especially also in large volumes. The use of the non-typical methods according to this invention are especially effective for those not able to or not anxious to follow the historical procedures.

The invention applies equally to all types of body cells including ectodermal, mesodermal or endodermal derived cells. It also applies to all types of immune cells which may be of special relevance and which are known in the art and for instance mentioned in Dr. Paul's *Fundamentals of Immunology* and numerous other standard texts in the appropriate fields. It also applies to neural cells which are closely related to the immune system (The Neuro-Immunologic System) and are known in the art and for instance mentioned in Neurology. These include but are not limited to B. T, NK, macrophage, APC, killer, endothelial, fibroblastic, astrocytic cells and cells that support and aid the growth of these cells.

EXAMPLES

Example 1 shows effectiveness when included in juice. Beginning in 2002 work was commenced experimenting with preparations designed to provide delivery of the homeopathic medicine to internal regions. Unexpectedly it was discovered that dilution in a liquid, for example, orange juice, other juices or water and swallowing the dilution, resulting in delivery to the stomach and more distal digestive organs, was similarly effective as sublingual and much more palatable and convenient for certain persons such as, for instance, teenagers. Further, the presence of a wide variety of chemicals including acids and strong fruit flavors did not prevent the action of the homeopathic.

Example 2

Effectiveness with Food; Effectiveness Against Seizures

The homeopathic remedy may be included in food. For example, Misty, a cat who had been accepted by a rescue shelter, suffered with severe, potentially life-threatening Gran Mal seizures about three times a day and almost every other day. She was tried on a variety of herbal medications and on Bromide salts without significant benefits. Taurox SB™ was added to her food, and she promptly stopped having seizures. She has not had a seizure for 27 days. Overall, she averaged a few a month while being treated.

Example 3

Ingestion of Taurox in Water

R. J. S., a middle-aged woman who has suffered with respiratory allergies her entire life reported that taking 16 drops Integra TH™ containing homeopathics including Taurox SB™ in 8 ounces of water once a day reduced nasal congestion and increased her energy level.

Example 4

S. F., a woman who suffered with a stroke 1996, used Taurox SB™ (10 drops, Integra TH™) in a cup of water and found that the muscle fatigue on her left side was much reduced and her overall sense of well being increased. In addition, the relative ratio of effects of the homeopathic medicine on her overall constitution vs. her specific pain was altered.

Example 5

D. P., a man with persistent fatigue and mild depression, reported that ingesting Taurox SB™ in a glass of water (45 drops Integra TH™) in a day's time, produced a stimulating effect alleviating both the fatigue and mild depression even on the first day of usage.

Example 6

T. C., a 42 year old woman with Sickle Cell Anemia, reports that swallowing Taurox SB™ in a glass of water (15 drops Integra TH™) reduces the fatigue and pain of her disease.

The medication may be included, for example, in water or juice. Example 1, described above, shows the effectiveness when included in juice. However, it may also be included in water, sports drinks, pleasure drinks, including alcoholic and non-alcoholic drinks, slurries, gels or foods, which are all possible.

The homeopathic remedy may also be included in food. Misty had a history of Gran Mal seizures three times a day, almost every day. Since including Taurox SB™ in her food she had not had a seizure for 27 days. This invention applies to all foods from treats treated with the homeopathic on site, to the bulk supplied food while making it, to massive watering systems used to water livestock or irrigate fields. It applies to all forms of life including human, animal and plant.

From these examples, it can be clearly appreciated that these homeopathic drugs are effective when taken diluted in large volumes of a variety of solutes or solutions. The level of effectiveness and the exact range of effects may vary. The solute is expected to slow absorption and may have a relatively minor less than 10× effect on the apparent concentration.

The homeopathic may be mixed in water, carbonated water juices of various types or any liquid or semi-liquid or solid material. It may also be in a multicomponent material such as a micelle, micro-sphere or other material. It may be coated with special materials well known in the pharmaceutical art to limit absorption in the upper GI tract and target absorption to the intestines or lower GI tract which may be in need of therapy in a variety of diseases including Crohn's Disease, Ulcerative Colitis, cancer and inflammatory and infectious problems. Targeting to any organ or region in the body may be achieved with antibodies or specific binding materials.

Various doses may be used as known in the homeopathy art from 1× to 200M. The most preferred embodiments are 3× to 20× and especially 5× to 10×.

For some preparations, it has been beneficial to encapsulate the drug in capsule, or compact the same into a pill, to facilitate the task of carrying and administration, especially if it is being co-administered with a variety of nutraceuticals or pharmaceutical materials best, most commonly, or most conveniently given in a pill or capsule form.

Administration in large volume of water, sports drink, mineral or nutrient-containing water or other drink may be especially advantageous as it spreads out the administration over the period of time as the drink is consumed.

Thus these new methods may have pharmacokinetic, pharmacodynamic and convenience advantages.

Administration of Taurox in small volumes sublingually or especially by nasal spray or eye wash spray has been found recently to assist in CNS problems including fatigue, weakness and seizures. Treatment of CNS with Taurox SB™ is therefore another aspect of this invention. Similar results have been observed when administered in large volumes of liquid.

Administration of Taurox SB™ in a variety of methods may decrease pain and damage due to sickle cell anemia, arteriole or artery blockage and pulmonary hypertension when given in a variety of doses and dose forms. Treatment of Sickle Cell Anemia with Taurox SB™ is thus another discovery that is part of this invention.

The invention, although illustrated for Taurox SB™, applies to all homeopathic remedies whether used as single agents of mixtures, regardless of their function. For example, cold remedies, remedies for fatigue such as the Dolisos product, remedies for flu and any other types may be given in this larger form. This is in stark contrast to previous teachings of both low volume and the need described in homeopathic texts to limit the intake of other materials within a period of time before or after the taking of the homeopathic.

What is claimed is:

1. A method for administering homeopathic preparations, comprising the step of targeting the absorption of a volume of at least ½ oz. the preparation to non-nasopharyngeal oral and non-nasopharyngeal regions, wherein the homeopathic preparation is prepared by serial dilution and succussion of a solution initially containing a carbo-benzoxy beta-alanyl taurine compound, and the preparation is administered to a subject to aid in improving CNS function, stimulating the immune system, relieving fatigue, improving concentration, increasing endurance, treating viral infections, treating seizures, treating allergies, treating depression, or treating pain and fatigue associated with sickle cell anemia.

2. A method according to claim 1, wherein the regions are in the digestive system.

3. A method according to claim 1, wherein the regions contain Mucosal Associated Lymphocytic Tissues.

4. A method according to claim 2, where the regions include the stomach, the small intestine and the large intestine proximal to the rectum.

5. A method of claim 1, in which the homeopathic preparation is mixed with a liquid minutes to 24 hours in advance of administration.

6. A method of claim 4, in which the homeopathic preparation is mixed days, months, years, or weeks in advance.

7. A method of claim 1, wherein the homeopathic preparation is swallowed.

8. A method of claim 1 in which the homeopathic preparation is mixed with other homeopathies, nutraceuticals, pharmaceuticals, active, carrier or inactive agents.

9. A method of claim 1, wherein the preparation is administered to improve CNS function.

10. The method of claim 1, wherein the preparation is administered to a subject to aid in relieving fatigue.

11. The method of claim 1, wherein the preparation is administered to a subject to aid in treating viral infections.

12. A method for administering a volume of at least ½ oz. of homeopathic preparations, comprising the step of targeting the absorption of the preparation to non-nasopharyngeal oral and non-nasopharyngeal regions, wherein the homeopathic preparation is prepared by serial dilution and succussion of a solution initially containing a carbo-benzoxy beta-alanyl taurine compound, and the homeopathic preparation is administered to a subject to aid in reducing the incidence of allergies or an allergic reaction.

13. A method for administering a volume of at least ½ oz. of homeopathic preparations, comprising the step of targeting the absorption of the preparation to non-nasopharyngeal oral and non-nasopharyngeal regions, wherein the homeopathic preparation is prepared by serial dilution and succussion of a solution initially containing a carbo-benzoxy beta-alanyl taurine compound, and the preparation is administered to a subject to treat or reduce the incidence of viral infection.

14. A method for administering a volume of at least ½ oz. of homeopathic preparations, comprising the step of targeting the absorption of the preparation to non-nasopharyngeal oral and non-nasopharyngeal regions, wherein the homeopathic preparation is prepared by serial dilution and succussion of a solution initially containing a carbo-benzoxy beta-alanyl taurine compound at low or high potency from 1× to 500 Million, and the preparation is administered to a subject to aid in improving CNS function, stimulating the immune system, relieving fatigue, improving concentration, increasing endurance, treating viral infections, treating seizures, treating allergies, treating depression, or treating pain and fatigue associated with sickle cell anemia.

* * * * *